United States Patent [19]

Sekine et al.

[11] Patent Number: 5,380,715

[45] Date of Patent: Jan. 10, 1995

[54] AP4A AS A HYPOTENSIVE AGENT

[75] Inventors: Akihiro Sekine; Yoshinori Kikuta; Shinkichi Tezuka; Kazuo Okada, all of Tokyo; Hiroshi Nakajima, Uji, all of Japan

[73] Assignees: Fujirebio Inc., Tokyo; Unitika Ltd., Amagasaki, both of Japan

[21] Appl. No.: 22,268

[22] Filed: Feb. 25, 1993

[30] Foreign Application Priority Data

Apr. 6, 1992 [JP] Japan .................................. 4-113111

[51] Int. Cl.$^6$ ............................................. A61K 31/70
[52] U.S. Cl. .................................. 514/47; 536/26.21; 536/26.22; 514/46
[58] Field of Search .......................... 536/26.21, 26.22; 514/46, 47

[56] References Cited

U.S. PATENT DOCUMENTS 3,321,463  5/1967  Moffatt et al. .................... 536/26.21

FOREIGN PATENT DOCUMENTS 0247819 12/1987  European Pat. Off. ......... 536/26.21
8904321  5/1989  WIPO .................................. 514/47

OTHER PUBLICATIONS

Luthje et al. (I), "Diadenosine Triphosphate (Ap3A) Mediates Human Platelet Aggregation by Liberation of ADP," *Biochem. Biophys. Res. Comm.* 118(3), 704–709 (1984).

Luthje et al.(II), "Catabolism of Ap3A and Ap4A in Human Plasma," *Eur. J. Biochem.*, 149, 119–127 (1985).

Blackburn et al., "Synthesis and Resistance to Enzymatic Hydrolysis of Stereochemically-Defined Phosphonate and Thiophosphate Analogues of P$^1$, P$^4$-bis(-5'-adenosyl)tetraphosphate," *Nucleic Acids Research*, 15(17), 6991–7004 (1987).

Harrison et al., "Inhibition of Platelet Aggregation and the Platelet Release Reaction by α,ωDiadenosine·Polyphosphates," *FEBS Letters*, 54(1), 57–60 (1975).

Elmaleh et al., "$^{99m}$Tc–labeled Nucleotides as Tumor-Seeking Radiodiagnostic Agents," *Proc. Natl. Acad. Sci. USA*, 81, 918–921 (1984).

"Metabolism of Diadenosine Tetraphosphate (Ap4A)," Conference Abstracts published in *Hoppe-Seyler's Z Physiol Chem.*, 365, S597–611 (1984).

Guranowski et al., "Phosphonate Analogues of Diadenosine 5', 5'''-Tetraphosphate as Substrates or (List continued on next page.)

*Primary Examiner*—John W. Rollins
*Assistant Examiner*—L. Eric Crane
*Attorney, Agent, or Firm*—Oblon, Spivak, McClelland, Maier & Neustadt

[57] ABSTRACT

A deliberated hypotensive agent is composed of diadenosine 5', 5'''-p$^1$,p$^4$-tetraphosphate with formula (I) or a salt thereof for which administration is medically permissible in an effective amount:

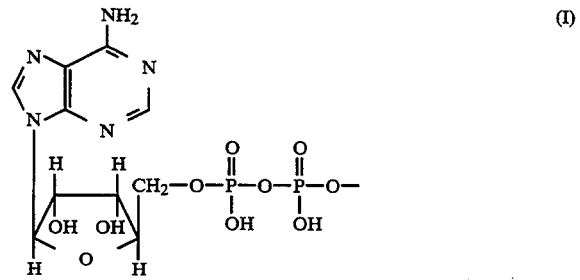

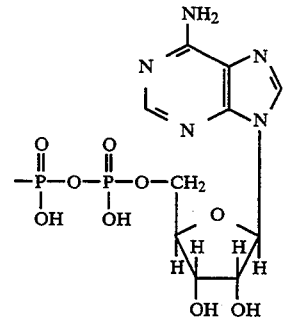

3 Claims, 5 Drawing Sheets

OTHER PUBLICATIONS

Inhibitors of Procaryotic and Eucaryotic Enzymes Degrading Dinucleoside Tetraphosphates," *Biochemistry*, 26, 3425–3429 (1987).

Feldhaus et al., "Synthetic Inhibitors of Adenylase Kinase in the Assays for ATPases and Phosphokinases," *Eur. J. Biochem.*, 57(1), 197–204 (1975); Chem. Abstr., 83:159.849u (1975); only Abstract provided.

Taursova et al., "The Synthesis of $P^1,P^3$-bis(-5'-Adenosyl)triphosphate, $P^1$, $P^4$-bis(5'-Adenosyl)tetraphosphate and Its Phosphonate Analogues Using Carbonyl Derivatives on Nitrogen-Containing Heterocycles," *Bioorg. Khim.*, 12(3), 404–407 (1986); Chem. Abstr., 105: 227,203e (1986); only Abstract provided.

Fukunaga et al., "Hypotensive Effects of Adenosine and Adenosine Triphosphate Compared with Sodium Nitroprusside," *Anesthesia and Analgesia*, 61, 273–278 (1982).

Busse et al., "Vasomotor Activity of Diadenosine Triphosphate and Diadenosine Tetraphosphate in Isolated Arteries," *Am. J. Physiol.*, 254(5), H828–H832 (1988).

Nees, "Coronary Flow Increases Induced by Adenosine and Adenine Nucleotides Are Mediated by the Coronoray Endothelium: A New Principle of the Regulation of Coronary Flow," *European Heart J.*, 10, Supplement F, 28–35 (1989).

"Martindale, The Extra Pharmacopoeia, 29th Ed." Reynolds et al. eds., The Pharmaceutical Press, London, 1989, at p. 1492, see entries for AMP (#9201-m) and ATP (#9203-v).

Sollevi et al., "Relationship Between Arterial and Venous Adenosine Levels and Vasodilation During ATP- -and Adenosine Infusion in Dogs," *Acta Physiol. Scand.*, 120, 171–176 (1984).

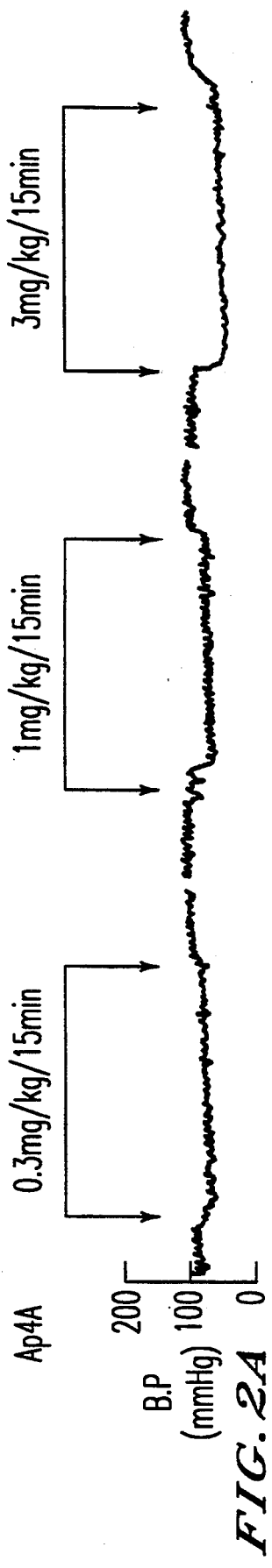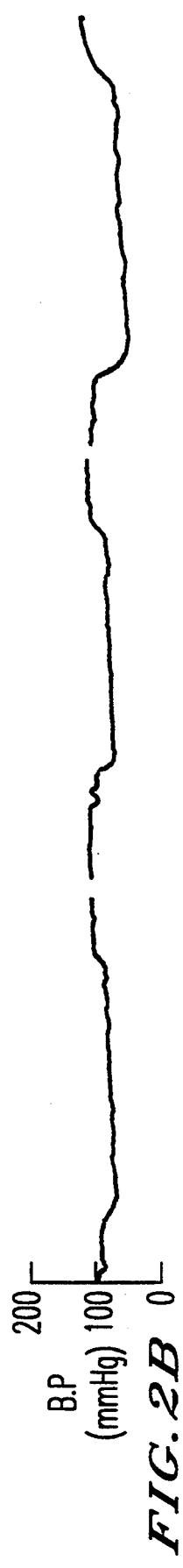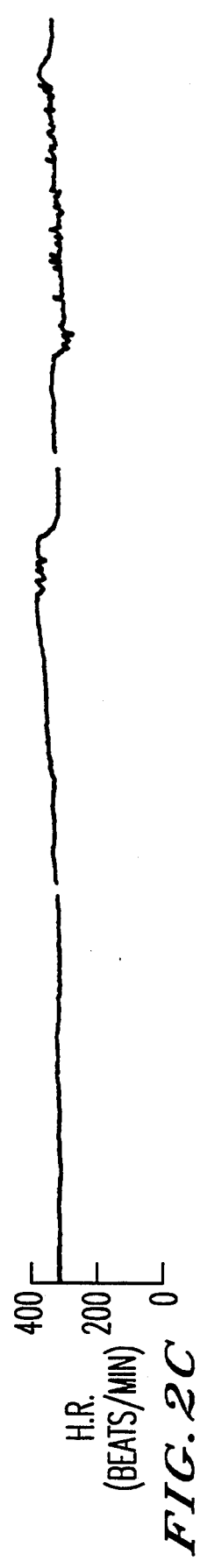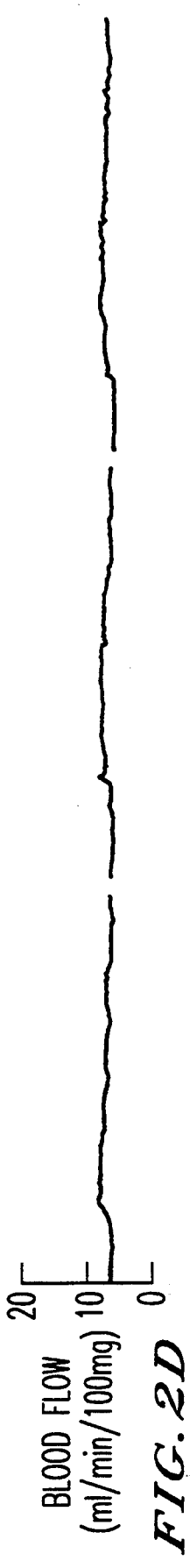

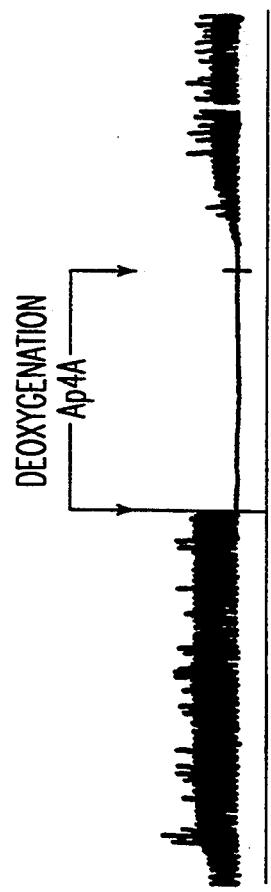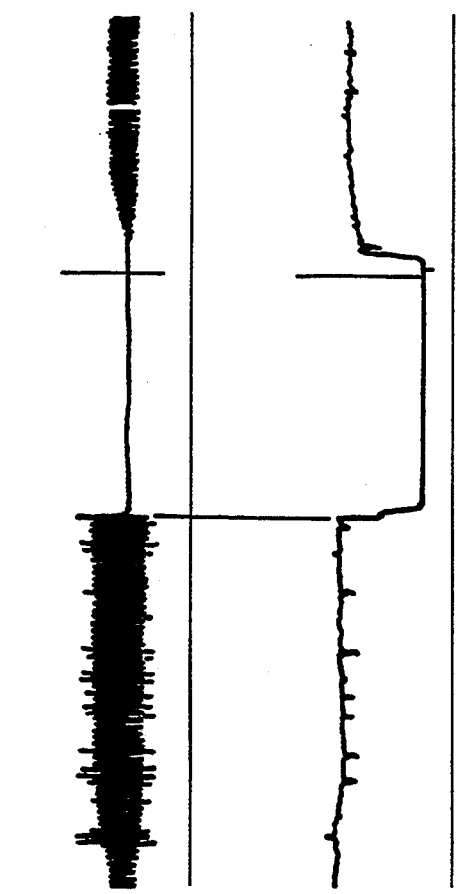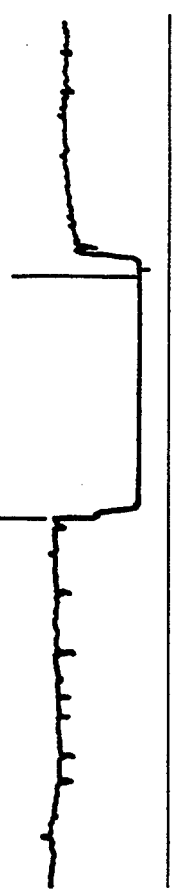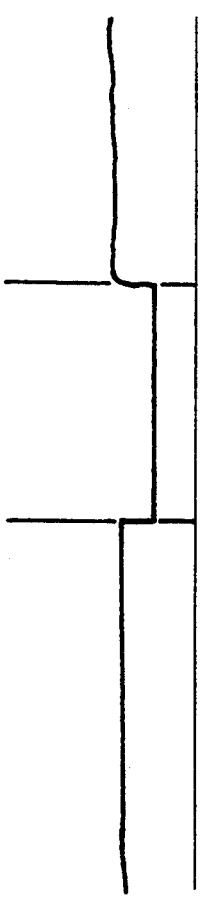

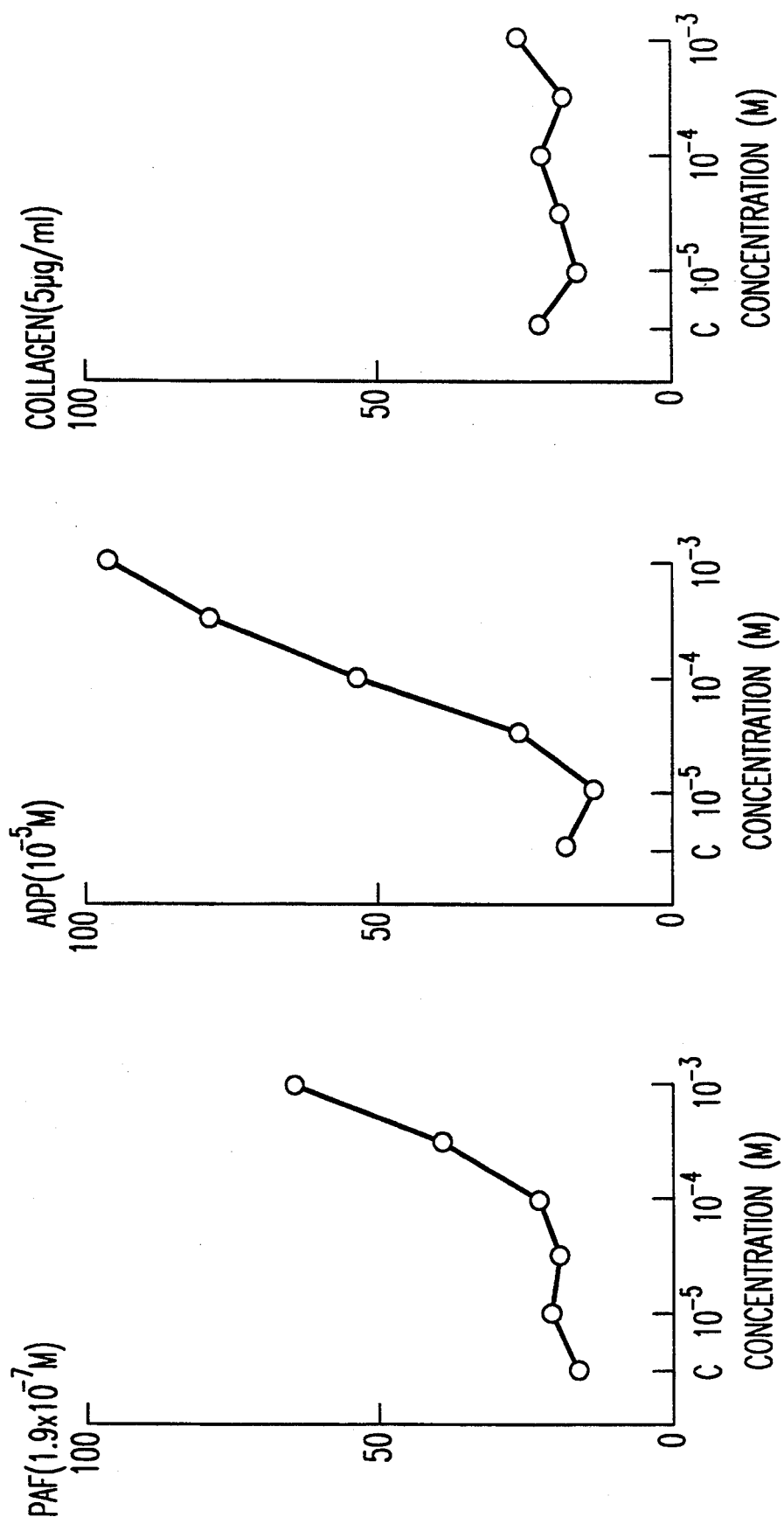

AP4A AS A HYPOTENSIVE AGENT

BACKGROUND OF THE INVENTION

1. Field of the Invention

The present invention relates to a deliberated hypotensive agent comprising diadenosine 5', 5'''-p$^1$,p$^4$-tetraphosphate or a salt thereof.

2. Discussion of Background

Since around 1940, hypotensive anesthesia has been applied in various surgeries to make surgical operations easy and to decrease surgical blood loss during surgery.

The clinical advantages of hypotensive anesthesia are that the amount of blood transfusion can be reduced, risks accompanied by blood transfused can be minimized, and surgical operation time can be decreased by producing a drier surgical field. Because of these advantages and other advantages, hypotensive anesthesia is now employed in various surgeries (Fumio Goto et al., The Japanese Journal of Anesthesiology, 2, 199, 1983).

Hypotension can be produced by various methods. For example, in early 1930s, a method of discharging a large amount of blood from the body, and spinal cord anesthesia, extradural anesthesia, halothane anesthesia, and combinations thereof will deep anesthesia were conducted. However, when blood pressure is artificially decreased by discharging blood with deep anesthesia, circulation failure of vital organs such as brain, heart and kidney, can develop (D. M. Little, Anesthesiology 16, 320, 1955; A. G. Larson, Anesthesiology, 25, 682, 1964). For this reason, trimethaphan (Trademark "Arfonad") is now used in combination with general anesthesia. Trimethaphan has excellent blood pressure regulation effect. However this effect lasts for a relatively long period of time, so that cardiac contractility, cardiac output, and coronary blood flow are decreased by the ganglionic blockade thereof and histamine liberation effect is increased. Furthermore, trimethaphan has the shortcomings that administration of a large amount of trimethaphan causes renal insufficiency because of tubular impairment near the kidney, tachyphylaxis, tachycardia, and mydriasis after its use. As a result, a significant improvement in hypotensitive anesthesia by deep anesthesia has not been attained (J. A. Agnilar and E. B. Boldrey, Anesthesiology 21, 3, 1960; A. G. Larson, Anesthesiology 25, 682, 1964; G. G. Rowe et al., Anesthesiology 25, 156, 1964).

Sodium nitroprusside and nitroglycerin were then tried. These have an excellent blood pressure regulation effect and are effective in maintaining coronary circulation accurately. Sodium nitroprusside, however, has fatal shortcomings in that it can cause histotoxic-anoxia-induced metabolic acidosis (Masaya Nakamura, Fukuoka Acta Medica 67, 514, 1976), and the cyanide contained in the compound is liberated within the body to induce cyanide poisoning (D. W. Davies et al., Canad. Anaeths. Soc. J. 22, 553, 1975; C. J. Vesey et al., Br. Med. J. 22, 140, 1974).

On the other hand, it has been pointed out that nitroglycerin has the shortcomings that congestion by the expansion of vanation, and tachycardia are caused (N. R. Fahmy, Anesthesiology 49, 17, 1978), sthenia of brain pressure is caused (S. Doli et al., Anesthesiology 54, 511, 1981), and the arterial oxygen tension (PaO$_2$) is decreased during hypotensive anesthesia (M. D. Oliverira et al., Br. J. Anaesth. 53, 11, 1981).

For these reasons, at present, nitroglycerin or prostaglandin E$_1$ (hereinafter referred to as PG E$_1$) is used in combination with general anesthesia.

At present, halothane is well known as an anesthetic for general anesthesia used under hypotensive anesthesia. Halothane anesthesia exhibits only a slight inhibitory effect on the circulation, but when surgery is extended for a long period of time, it causes hepatotoxicity and sthenia of brain pressure (S. Doli et al., Anesthesiology 54, 511, 1981; Tsutomu Mitsufuji et al., Anesthesia 31, 1102, 1982). Therefore, NLA (neuroleptannalgesia) is frequently used in surgery. However, NLA also frequently causes hypertension during surgery in the same manner as in the case of halothane anesthesia, so that control of its use is important. Furthermore, when halothane anesthesia is applied, hypertension is also caused by psychological stress before and after surgery.

In contrast to the above-mentioned anesthesia, hypotensive anesthesia has the advantages that blood loss can be minimized, surgery is made easier, and the stress induced by anesthetics and surgery can be minimized.

It is required that a deliberated hypotensive agent used during anesthesia show the following performance:

1. Excellent blood pressure regulation performance. Rapid onset of action upon the initiation of the administration, adequate control of blood pressure and rapid reversibilty upon the termination of the administration can be attained.
2. Production of decreased blood pressure regardless of the kind of anesthetic employed.
3. No decrease in blood flow into vital organs such as heart, liver, kidney, and brain under anesthesia.
4. No adverse effects on heart (i.e., no decrease in cardiac output, and no changes in heart rate and electrocardiogram).
5. Without causing tachyphylaxis.
6. Without causing rebound hypertension.
7. Without causing tachycardia.
8. Without increasing brain pressure.
9. Without causing acidosis.
10. Without decreasing gas tension in blood.
11. Without causing serious side effects.

SUMMARY OF THE INVENTION

It is therefore an object of the present invention to provide a deliberated hypotensive agent from which the shortcomings of the conventional hypotensive agents have been eliminated and which substantially satisfies the previously mentioned requirements for a deliberated hypotensive agent used during anesthesia.

The above object of the present invention can be achieved by a deliberated hypotensive agent comprising diadenosine 5', 5'''-tetraphosphate or salt thereof for which administration is medically permissible in an effective amount.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 2 is a graph showing the changes in the blood pressure (B.P.), heart rate (H.R.), and cerebral blood flow (C.B.F.) of rats anesthetized with urethane +α-chloralose under the continuous aministration of Ap4A.

FIG. 4 is a graph showing the protective effect of Ap4A on deoxygenation-induced cardiac damage which was treated with Ap4A, in which L.V.P denotes left ventricle pressure, dp/dt, rising rate, and H.R., heart rate, and P.P, perfusion pressure.

FIG. 5 are graphs showing the platelet aggregate dispersing effect of Ap4A in which PAF denotes a platelet activation factor, and ADP denotes adenosine diphosphate.

DESCRIPTION OF THE PREFERRED EMBODIMENTS

Figure 1:
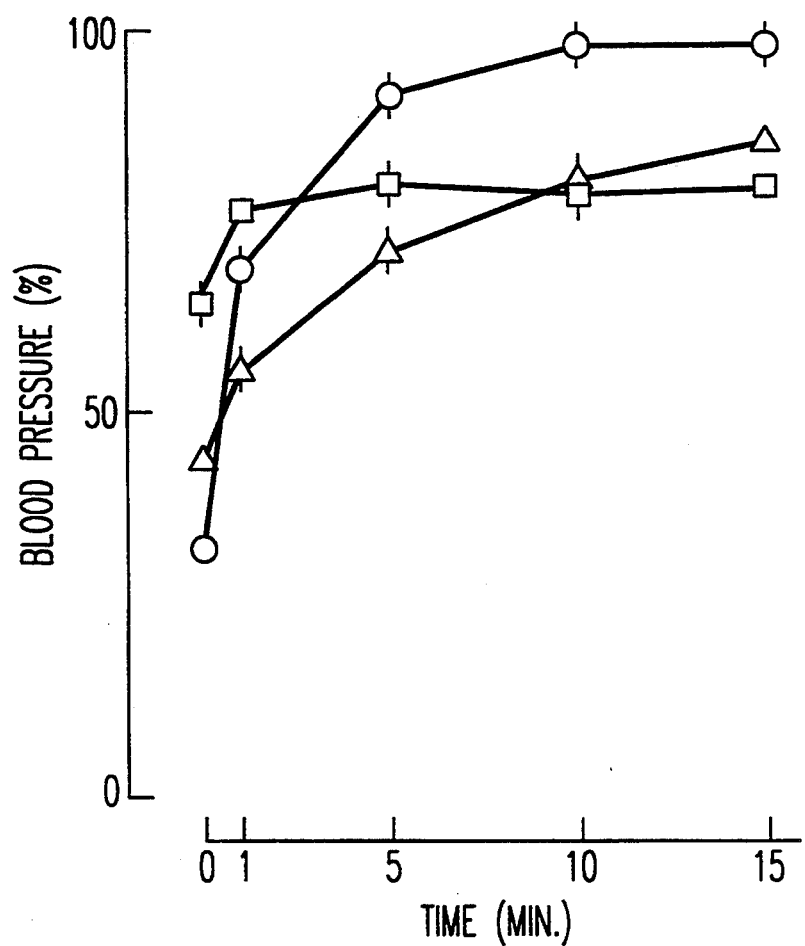
FIG. 1 is a graph showing the recovery of the blood pressure of rats anesthetized with enflurane with time, when each of Ap4A (●), PG E$_1$ (▲) and nitroglycerin (■) was used as a test drug to attain gradual hypotension, with the blood pressure before the administration of each test drug being set 100% for reference.
Figure 3A:
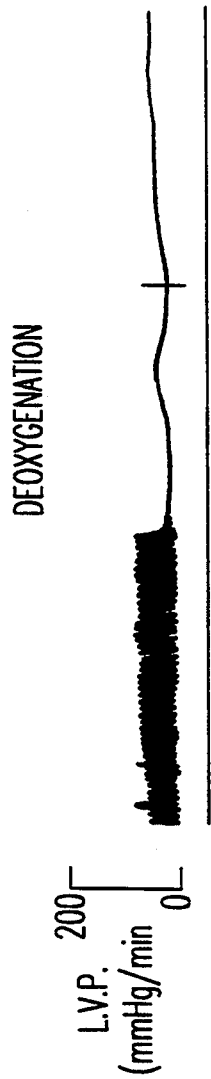
FIG. 3 is a graph showing the deoxygenation-induced cardiac damage of a Langendorff heart which was not treated with Ap4A, in which L.V.P denotes left ventricle pressure, dp/dt, rising rate, and H.R., heart rate, and P.P, perfusion pressure.
Figure 3B:
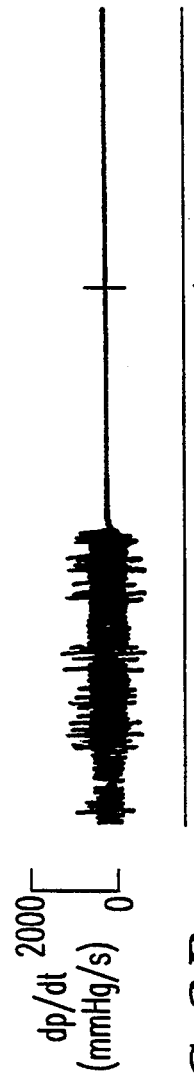
Figure 3C:
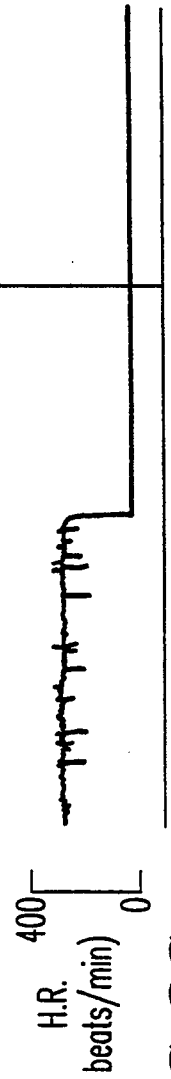
Figure 3D:
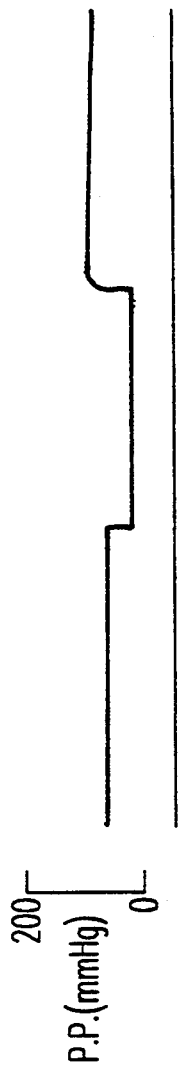

The deliberated hypotensive agent according to the present invention comprises diadenosine 5',5'''-p$^1$,p$^4$-tetraphosphate or a salt thereof for which administration is medically permissible, in an effective amount.

The diadenosine 5',5'''-p$^1$,p$^4$-tetraphosphate (hereinafter referred to as Ap4A) is a novel type of nucleotide present in the body, having the following structural formula:

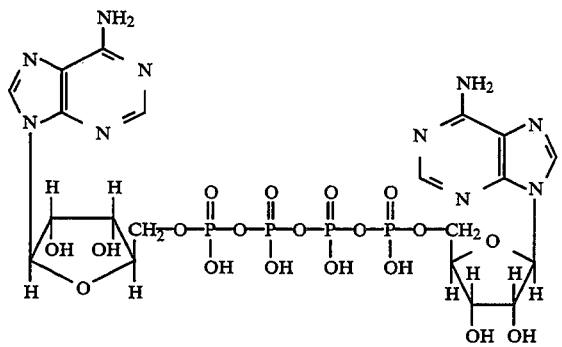

Ap4A can be produced by a conventionally known organic synthesis, using ATP as a starting material, and by an enzyme synthesis using aminoacyl tRNA synthetases, for example, bacillus-stearothermophilus-induced leucyl tRNA synthetase (Japanese Laid-Open Patent Application 62-288992). The 50% lethal dose (LD$_{50}$) of Ap4A measured by the Lichfield-Willcoxon Method is 102 mg/kg (rat intravenous injection), so that the toxicity of Ap4A is extremely low.

With respect to the bioactivities of Ap4A, for example, an ADP-induced human platelet-aggregation inhibitory effect (J. Leuthje and A. Ogiluie, Biochem. Biophys. Res. Commun., 118, 704, 1984), a vasodilating effect of rabbit mesenteric arteries (R. Buss et al., Am. J. Physiol., 254, 828, 1988), and an arrhythmic effect (Japanese Laid-Open Patent Application 3-187126) have been reported.

However, nothing has been reported about the possibility that Ap4A can be used as a deliberated hypotensive agent, although there was a report describing the use of a vasodilator as a deliberated hypotensive agent. However, not all vasodilators can be used as deliberated hypotensive agents because a deliberated hypotensive agent must meet the previously mentioned requirements 1 to 11.

It has been known that Ap4A has a vasodilation effect, but it has not been known that Ap4A can be used as a deliberated hypotensive agent.

The effectiveness of Ap4A as a deliberated hypotensive agent during anesthesia has been proved by a comparative test in which the conventionally known nitroglycerin (commercially available under the trademark "Millisrol") and a cathrate of PG E$_1$ (commercially available under the trademark "prostandin 500") were compared with Ap4A.

Hemodynamic Effects of Gradual Hypotension Induced by Ap4A, PG E$_1$, and Nitroglycerin in Dogs Dogs were anesthetized with enflurane. By use of each of Ap4A, PG E$_1$, and nitroglycerin, the blood pressure thereof was gradually decreased. The mean blood pressure (B.P.), heart rate (H.R.), cardiac output (C.O.), arterial oxygen tension (PaO$_2$), mixed venos oxygen tension (PvO$_2$), arterial carbonate tension (PaCO$_2$), mixed venous carbonate tension (PvCO$_2$), arterial pH (pH-a), mixed venous pH (pH-v), and base excess thereof were measured. The results are shown in Tables 1 to 3.

It is possible to gradually decrease blood pressure by Ap4A, and the onset of the action thereof is very rapid. In order to attain an 80% fall in blood pressure, a large amount of Ap4A is required. This indicates that Ap4A is a very safe drug. The gradual hypotensive effect of Ap4A is comparable with that of PG E$_1$ and is better than that of nitroglycerin which can attain only about a 30% fall in blood pressure.

It can be predicted that artificial hypotension during anesthesia will be about a 40% fall in blood pressure. However, since the dose of Ap4A which exhibits a significant effect on heart rate is that required for a 60% or more fall in blood pressure, the decrease of cardiac function does not become a problem.

Although nothing is shown in Table 2, PG E$_1$ exhibits a tendency to increase the heart rate when a 20% or less fall in blood pressure is attained. This indicates the possibility that PG E$_1$ induces tachycardia even if the tachycardia is slight, although no specific data is given.

Nitroglycerin exhibits a tendency to increase the heart rate when a 20% fall in blood pressure is attained, so that it is considered that tachycardia will be induced by nitroglycerin.

Ap4A also exhibits a tendency to significantly increase the cardiac output when a 20% fall in blood pressure is attained, and the cardiac output is continuously increased until a 60% fall in blood pressure is attained. This effect is much more conspicuous than the effects of PG E$_1$ and nitroglycerin which are said to sufficiently maintain coronal blood flow. This proves that Ap4A can significantly maintain coronary blood flow and the effect is considered to be one of the excellent effects of Ap4A.

Furthermore, Ap4A exhibits a tendency to increase arterial oxygen tension (PaO$_2$), and mixed venous oxygen tension (PvCO$_2$), or actually increases PaO$_2$ and PvO$_2$, and exhibits a tendency to decrease arterial carbonate tension (PaCO$_2$), mixed venous carbonate tension (PvCO$_2$), or actually decreases PaCO$_2$ and PvCO$_2$. This proves that Ap4A maintains the gas exchange and oxygen consumption in vital organs in a normal condition, thereby protecting vital organs.

In sharp contrast to this, PG $E_1$ has almost no effects on the oxygen tension and carbonate tension, and nitroglycerin, on the contrary, decreases $PaO_2$.

Ap4A does not substantially decrease arterial pH in practical use. This means that little acidosis is caused by Ap4A. In contrast to this, PG $E_1$ and nitroglycerin significantly decrease arterial pH or have a tendency to decrease arterial pH, so that it is considered that PG $E_1$ and nitroglycerin may cause acidosis.

The same results as mentioned above were obtained with respect to rats as shown in Table 4. This indicates that the hypotensive effect can be attained by Ap4A regardless of the kind of mammalians.

Furthermore, Ap4A can also attain almost the same gradual hypotensive effect even when halothane anesthesia and urethane (0.5 g/kg) +α-chloralose (80 mg/kg) anesthesia are employed. This suggests that the blood pressure decreasing effect of Ap4A is independent of the kind of anesthetic employed.

The recovery of blood pressure after gradual hypotension by use of each of Ap4A, PG $E_1$ and nitroglycerin was also tested. The rapidness of the recovery was in the order of Ap4A>PG $E_1$>nitroglycerin. With respect to Ap4A, the blood pressure did not exceed the blood pressure (100%) before the administration thereof, so that it was confirmed that Ap4A is a deliberated hypotensive agent with an excellent blood pressure regulation performance, without rebound hypertension, as shown in FIG. 1.

Effects of Ap4A on Cerebral Blood Flow

Cerebral blood flow (C.B.F) was found to be improved by bolus injection of Ap4A in a slightly smaller amount than or in substantially the same amount as that for producing decreased blood pressure as shown in Table 5. Cerebral blood flow was increased during continuous administration of Ap4A as shown in FIG. 2.

Protective Effective of Ap4A on Deoxygenation-induced Cardiac Damage

The protective effect of Ap4A against ischemia by use of a Langendorff heart (Aronson, CE. and Serlick, ER. Toxicol. Appl. Pharmac. 38, 479–488 (1976)) was tested.

In a reference test using a Langendorff heart which was not treated with Ap4A (refer to FIG. 3), a 33-minute ischemic state caused the left ventricle pressure (L.V.P.), rising rate (dp/dt), and heart rate (H.R.) to disappear and had adverse effects on the Langendorff heart. In contrast to this, in the case of a Langendorff heart treated with Ap4A, the above-mentioned impairment in the untreated Langendorff heart was found to be prevented as shown in FIG. 4. This suggests that even if a slight ischemic state is produced, Ap4A has a protective effect against this state.

Platelet Aggregation Inhibitory Effect and Platelet Aggregation Dispersion Effect Ap4A inhibits ADP-induced and Ap3A (diadenosine 5', 5'''-p$^1$,p$^4$-triphosphate)-induced platelet-aggregation reactions as shown in Table 6. The inhibitory effect of Ap4A is considered to be rapid because a substantially maximum effect is obtained within one minute.

Furthermore, it has been discovered that Ap4A also has the function of dispersing aggregated lumps formed by PAF (platelet activating factor) and ADP as shown in FIG. 5.

These results suggest that Ap4A is useful as a deliberated hypotensive agent that can be used during surgery for diseases accompanied by a thrombotic disease. Furthermore, the platelet aggregation inhibitory effect of Ap4A suggests that Ap4A can be used for the improvement of peripheral circulation.

Effects of Ap4A on Erythrocyte Crenation

Ap4A was found to have a significant inhibitory effect on a calcium inonophore A23187 induced erythrocyte crenation as shown in Table 7. This effect of Ap4A indicates the promotion of the improvement of peripheral circulation.

As mentioned previously, Ap4A can attain a rapid onset of action upon the initiation of the administration and can maintain a desired blood pressure, and also can attain rapid reversibility upon the termination of the administration. It was found that Ap4A can provide extremely excellent control of blood pressure. The hypotension attained by Ap4A during anesthesia is not affected by the kind of anesthetic employed. This suggests that even when Ap4A is administered in such an amount as to produce hypotension, the blood flow into the heart and brain is increased, and no adverse effects are caused on the heart (i.e. increase in cardiac output, and no changes in heart rate). No acidosis and no decrease in the $O_2$ and $CO_2$ tensions in the blood are caused. Furthermore, this suggests that Ap4A causes no tachyphylaxis, rebound hypertension and tachycardia.

The deliberated hypotensive agent according to the present invention is also effective for hypertension caused by psychological stress before and after surgery and anesthetic used during surgery, and for curing general hypertension.

As mentioned previously, the deliberated hypotensive agent according to the present invention comprises diadenosine 5', 5'''-p$^1$,p$^4$-tetraphosphate or a salt thereof which can be medically administered, in an effective amount.

Examples of the salt include alkali metal salts, alkaline earth metal salts, ammonium salts, and organic amine salts. Preferable examples of the salts are alkali metal salts, in particular, sodium salts. The salts include all and partial salts of the phosphate groups of diadenosine 5', 5'''-p$^1$,p$^4$-tetraphosphate.

The term "effective amount of Ap4A" means such an amount of Ap4A as can induce hypotension during anesthesia in human and other mammalians. Generally the term means such an amount that decreases the blood pressure by less than 50%, preferably 40% or less, of the mean arterial pressure before the administration of Ap4A. The dose of Ap4A can be changed depending upon the age, symptom, weight, and other factors of the patient, which are recognized by those skilled in the art.

The deliberated hypotensive agent according to the present invention may further comprise a carrier and a diluent which are medically permissible. An example of such a carrier is cyclodextrin, and examples of such a diluent are liquids for transfusion, for example, physiological saline, water for injection, and sterile purified water.

The deliberated hypotensive agent according to the present invention may further comprise conventionally employed additives such as a stabilizer, isotonicity, solubilizing agent, preservative and buffer.

The deliberated hypotensive agent may be in the form of either a solid or a liquid. In the case of a solid, the hypotensive agent can be dissolved in an appropriate liquid carrier such as physiological saline and administered together with a parenteral solution or a dripping liquid. In the case of a liquid, the hypotensive agent can be formulated in the form of an injection or a dripping liquid, and administered by intravenous injection.

Other features of this invention will become apparent in the course of the following description of exemplary embodiments which are given for illustration of the invention and are not intended to be limiting thereof.

Example 1

[Gradual Hypotension during Anesthesia Induced by Ap4A in Dogs]

Mongrel dogs weighing 9 to 17 kg were anesthetized with intravenous thiopental 20 mg/kg by bolus injection, followed by 1% enflurane in 40% $O_2/N_2$ after endotracheal intubation. After muscle relaxation was achieved with pancuronium, the dogs were ventilated with a ventilator to maintain end-tidal carbon dioxide ($CO_2$) concentration at 37–41 mmHg. Bilateral femoral arteries were catheterized, one for the determination of blood pressure and the other for blood sampling.

Access to the bilateral femoral veins was obtained for the administration of Ap4A, PG $E_1$ or nitroglycerin and for the insertion of a ballon-tipped thermodilution catheter. The electrocardiogram was continuously monitored. The control values were obtained before the administration of each of the above-mentioned three agents. Each agent was administered using a syringe pump at titrated doses to produce gradual 20%, 40%, 50%, 60%, and 80% decreases in the mean arterial pressure (MAP) from the control value.

After the target blood pressure and stable hemodynamic conditions were reached, the following parameters were measured: heart rate (HR), mean pulmonary artery pressure (PAM), pulmonary capillary wedge pressure (PCWP), and central venous pressure (CVP). Cardiac output (CO) was determined by the thermodilution method. Gas analyses of arterial and mixed venous bloods were performed using a blood gas analyzer.

Table 1 shows the results of the hemodynamic effect of gradual hypotension induced by Ap4A in the dogs.

Table 2 show the results of the hemodynamic effect of gradual hypotension induced by a dichlorodextrane clathrate of PG $E_1$ (commercially available under the trademark "prostandin 500" from Ono Pharmaceutical Co., Ltd.) in the dogs.

Table 3 show the results of the hemodynamic effect of gradual hypotension induced by nitroglycerin (commercially available under the trademark "millisrol" from Nippon Kayaku Co., Ltd. ) in the dogs.

TABLE 1

| Hemodynamic effect of gradual hypotension induced by Ap4A in dogs (N = 9) | | | | | | |
|---|---|---|---|---|---|---|
| Blood Pressure (−Δ%) | 0 | −20% | −40% | −50% | −60% | −80% |
| Dose (μg/kg/min) | 0 | 72.5 ± 8.8 | 137.9 ± 15.8 | 163.4 ± 24.3 | 242.4 ± 32.8 | 3895.2 ± 675.7 |
| Mean Blood Pressure B.P. | | | | | | |
| (mean) | 130.1 ± 4.4 | 104.3 ± 3.3 | 78.2 ± 2.3 | 65.4 ± 2.0 | 51.7 ± 1.7 | 28.8 ± 1.0 |
| (Δ%) | 0 | −19.8 ± 0.4 | −39.8 ± 0.4 | −49.6 ± 0.4 | −60.3 ± 0.2 | −77.8 ± 0.8 |
| Heart Rate H.R. (beats/min) | 161.9 ± 6.7 | 160.1 ± 7.5 | 154.9 ± 6.9 | 144.0 ± 7.3 | 131.6 ± 7.5 | 98.6 ± 4.7 |
| Pulmonary Artery Pressure PAM (mmHg) | 16.6 ± 1.6 | 18.4 ± 1.5 | 17.8 ± 1.6 | 16.3 ± 1.4 | 14.3 ± 1.1 | 14.3 ± 1.2 |
| Pulmonary Capillary Wedge Pressure PCWP (mmHg) | 8.3 ± 0.7 | 8.3 ± 1.3 | 8.0 ± 1.2 | 7.6 ± 1.2 | 6.7 ± 10.9 | 7.4 ± 1.0 |
| Central Venous Pressure CVP (mmHg) | 3.80 ± 0.29 | 3.77 ± 0.25 | 3.89 ± 0.29 | 3.64 ± 0.35 | 3.63 ± 0.44 | 3.51 ± 0.60 |
| Cardiac Output C.O. (L/min) | 1.78 ± 0.16 | 2.42 ± 0.25 | 2.22 ± 0.15 | 2.02 ± 0.16 | 1.55 ± 0.20 | 1.16 ± 0.11 |
| Body Temperature BT (°C.) | 37.3 ± 0.6 | 37.2 ± 0.6 | 37.3 ± 0.6 | 37.2 ± 0.6 | 37.2 ± 0.6 | 37.4 ± 0.6 |
| Arterial Oxygen Tension PaO2 (mmHg) | 250.5 ± 6.5 | 252.8 ± 7.2 | 253.8 ± 7.6 | 252.5 ± 7.5 | 253.8 ± 7.7 | 245.6 ± 9.2 |
| Mixed Venous Oxygen Tension PvO2 (mmHg) | 54.0 ± 2.3 | 61.6 ± 2.4 | 63.3 ± 1.7 | 60.5 ± 2.1 | 54.9 ± 1.8 | 53.3 ± 2.8 |
| Arterial Carbonate Tension PaCO2 (mmHg) | 37.2 ± 0.9 | 36.0 ± 1.0 | 35.3 ± 1.0 | 35.0 ± 1.1 | 34.6 ± 1.3 | 37.5 ± 1.1 |
| Mixed Venous Carbonate Tension PvCO2 (mmHg) | 41.4 ± 1.3 | 39.3 ± 1.2 | 36.6 ± 1.3 | 36.7 ± 1.4 | 38.1 ± 1.8 | 44.4 ± 1.4 |
| Arterial pH (pH-a) | 7.335 ± 0.011 | 7.337 ± 0.013 | 7.341 ± 0.018 | 7.338 ± 0.011 | 7.315 ± 0.010 | 7.260 ± 0.010 |
| Mixed Venous pH (pH-v) | 7.301 ± 0.010 | 7.308 ± 0.008 | 7.311 ± 0.009 | 7.308 ± 0.011 | 7.292 ± 0.011 | 7.228 ± 0.014 |
| Hematocrit Value Hct (%) | 38.8 ± 2.0 | 40.6 ± 2.1 | 40.6 ± 1.7 | 40.7 ± 1.7 | 41.9 ± 2.2 | 42.8 ± 2.2 |
| Base Excess BE (mBq-1) | −5.02 ± 0.54 | −5.39 ± 0.77 | −5.52 ± 0.89 | −5.77 ± 0.66 | −7.30 ± 0.64 | −9.36 ± 0.79 |

TABLE 2

| Hemodynamic effect of gradual hypotension induced by prostaglandin $D_1$ in dogs (N = 6) | | | | | |
|---|---|---|---|---|---|
| Blood Pressure (−Δ%) | 0 | −20% | −40% | −50% | −60% |
| Dose (μg/kg/min) | 0 | 1.66 ± 0.48 | 3.61 ± 1.01 | 4.77 ± 1.14 | 5.91 ± 1.49 |
| Mean Blood Pressure B.P. | | | | | |
| (mean) | 134.5 ± 6.9 | 107.2 ± 5.3 | 79.8 ± 4.6 | 67.5 ± 3.4 | 56.0 ± 4.3 |
| (Δ%) | 0 | −20.3 ± 0.4 | −40.7 ± 0.5 | −49.8 ± 0.2 | −58.1 ± 1.3 |
| Heart Rate H.R. (beats/min) | 171.3 ± 7.0 | 167.8 ± 8.6 | 155.5 ± 9.1 | 143.3 ± 7.3 | 134.6 ± 7.2 |
| Pulmonary Artery Pressure PAM (mmHg) | 16.5 ± 3.7 | 16.0 ± 3.8 | 13.3 ± 3.0 | 12.8 ± 2.7 | 12.4 ± 3.4 |

TABLE 2-continued

Hemodynamic effect of gradual hypotension induced by prostaglandin $D_1$ in dogs (N = 6)

| Blood Pressure (−Δ%) | 0 | −20% | −40% | −50% | −60% |
|---|---|---|---|---|---|
| Pulmonary Capillary Wedge Pressure PCWP (mmHg) | 9.2 ± 2.2 | 9.0 ± 3.0 | 6.8 ± 2.1 | 6.7 ± 2.0 | 6.2 ± 2.2 |
| Central Venous Pressure CVP (mmHg) | 3.98 ± 0.60 | 3.27 ± 0.59 | 3.12 ± 0.47 | 3.48 ± 0.56 | 3.70 ± 0.76 |
| Cardiac Output C.O. (L/min) | 1.46 ± 0.14 | 1.47 ± 0.18 | 1.20 ± 0.14 | 1.17 ± 0.11 | 1.04 ± 0.10 |
| Body Temperature BT (°C.) | 37.6 ± 0.6 | 37.4 ± 0.6 | 37.3 ± 0.6 | 37.2 ± 0.6 | 36.9 ± 0.7 |
| Arterial Oxygen Tension $PaO_2$ (mmHg) | 255.5 ± 7.6 | 251.6 ± 8.3 | 249.3 ± 6.0 | 251.7 ± 9.3 | 253.2 ± 11.92 |
| Mixed Venous Oxygen Tension $PvO_2$ (mmHg) | 47.1 ± 2.9 | 51.0 ± 1.0 | 50.0 ± 1.9 | 53.3 ± 4.5 | 49.9 ± 3.1 |
| Arterial Carbonate Tension $PaCO_2$ (mmHg) | 36.7 ± 0.8 | 37.3 ± 1.4 | 36.0 ± 0.7 | 36.9 ± 1.0 | 36.8 ± 1.0 |
| Mixed Venous Carbonate Tension $PvCO_2$ (mmHg) | 41.9 ± 1.4 | 41.3 ± 1.3 | 39.7 ± 1.0 | 41.6 ± 0.6 | 40.6 ± 1.2 |
| Arterial pH (pH-a) | 7.376 ± 0.009 | 7.323 ± 0.015 | 7.334 ± 0.012 | 7.303 ± 0.017 | 7.308 ± 0.022 |
| Mixed Venous pH (pH-v) | 7.333 ± 0.004 | 7.303 ± 0.009 | 7.286 ± 0.012 | 7.278 ± 0.015 | 7.275 ± 0.016 |
| Hematocrit Value Hct (%) | 38.2 ± 2.3 | 41.5 ± 2.9 | 39.8 ± 3.3 | 40.0 ± 3.5 | 38.4 ± 4.5 |
| Base Excess BE (mBq/l) | −2.65 ± 0.47 | −5.77 ± 0.77 | −5.55 ± 0.82 | −7.07 ± 1.14 | −6.78 ± 1.50 |

TABLE 3

Hemodynamic effect of gradual hypotension induced by nitroglycerin in dogs (N = 6)

| Blood Pressure (−Δ%) | 0 | −20% |
|---|---|---|
| Dose (μg/kg/min) | 0 | 42.2 ± 2.0 |
| Mean Blood Pressure B.P. (mean) | 124.3 ± 2.6 | 101.0 ± 1.5 |
| (Δ%) | 0 | −18.7 ± 0.9 |
| Heart Rate H.R. (beats/min) | 171.3 ± 9.1 | 191.7 ± 7.5 |
| Pulmonary Artery Pressure PAM (mmHg) | 15.2 ± 1.0 | 12.8 ± 1.0 |
| Pulmonary Capillary Wedge Pressure PCWP (mmHg) | 7.7 ± 1.1 | 8.0 ± 0.6 |
| Central Venous Pressure CVP (mmHg) | 2.20 ± 0.62 | 2.32 ± 0.75 |
| Cardiac Output C.O. (L/min) | 1.61 ± 0.21 | 1.58 ± 0.21 |
| Body Temperature BT (°C.) | 38.6 ± 0.3 | 38.6 ± 0.3 |
| Arterial Oxygen Tension $PaO_2$ (mmHg) | 239.7 ± 7.1 | 229.9 ± 2.7 |
| Mixed Venous Oxygen Tension $PvO_2$ (mmHg) | 47.4 ± 2.2 | 46.5 ± 2.7 |
| Arterial Carbonate Tension $PaCO_2$ (mmHg) | 35.1 ± 1.3 | 36.4 ± 1.6 |
| Mixed Venous Carbonate Tension $PvCO_2$ (mmHg) | 38.8 ± 1.7 | 39.6 ± 1.6 |
| Arterial pH (pH-a) | 7.352 ± 0.011 | 7.315 ± 0.020 |
| Mixed Venous pH (pH-v) | 7.321 ± 0.018 | 7.300 ± 0.014 |
| Hematocrit Value Hct (%) | 39.6 ± 3.0 | 42.2 ± 2.0 |
| Base Excess BE (mBq/l) | −4.90 ± 0.65 | −6.67 ± 0.71 |

Ap4A was capable of gradually decreasing the blood pressure in a dose-dependent manner up to about a 60% fall in blood pressure. For example, a 20% fall, 40% fall and 50% fall in blood pressure were respectively attained by a dose of about 70 μg/kg/min, a dose of about 140 μg/kg/min, and a dose of about 160 μg/kg/min. These results suggest that Ap4A has a conspicuous hypotensive effect. Furthermore, when a 60% or more fall in blood pressure is attained, Ap4A is seem to have significant adverse effects on the heart rate. Therefore, when the fall in blood pressure is less than 50%, there is no problem with Ap4A with respect to the decrease of cardiac function.

Furthermore, in the administration of Ap4A, cardiac output is significantly increased at a 20% fall in blood pressure and there is a tendency for the cardiac pressure to be increased up to a less than 60% fall in blood pressure.

Ap4A exhibits a tendency to increase arterial oxygen tension ($PaO_2$), and mixed venous oxygen tension ($PvO_2$), and a tendency to decrease arterial carbonate tension ($PaCO_2$), and mixed venous carbonate tension ($PvCO_2$). Furthermore, Ap4A does not decrease arterial pH and venous pH up to a less than 60% fall in blood pressure, and does not make any significant changes in base excess.

These results indicate that Ap4A has an excellent blood pressure regulation performance, causes little tachycardia and sufficiently maintains coronary blood flow. Furthermore, Ap4A maintains gas exchange and usage of oxygen in normal conditions and protects vital organs, causing little acidosis.

Ap4A exhibited the same hypotensive effect as that of PG $E_1$, but exhibited better results with respect to the blood gas analysis, acidosis, and excess base than PG $E_1$. Furthermore, Ap4A exhibited better results in various factors than nitroglycerin.

[Gradual Hypotension during Anesthesia Induced by Ap4A in Rats]

Male SD rats (Charles River Japan Inc.) were anesthetized with intravenous thiopental 50 mg/kg as a bolus, followed by 1% enflurane in air.

A femoral artery was catheterized to monitor the blood pressure and heart rate, while a femoral vein was catheterized for the administration of each of the test drugs.

The control values were obtained before the administration of each test drug. Each test drug was then administered using a syringe in a dose-dependent manner for 15 minutes. The percentage (%) of the decrease of blood pressure was determined when stabilized. Changes in heart rate (H.R.) at the administration of each test drug were measured. Furthermore, the recovery of mean blood pressure after intravenous infusion of each test drug was also determined from the decrease in heart rate and the blood pressure at a maximum dose of each test drug. The results are shown in Table 4 and FIG. 1.

through the hole, whereby the cerebral blood flow thereof was measured. A predetermined amount of

TABLE 4

Gradual hypotensive effect in rats

Blood Pressure

| Drug | N (μg/kg/min) | 1 | 3 | 10 | 30 | 100 | 300 | 1000 | 3000 |
|---|---|---|---|---|---|---|---|---|---|
| Ap4A | 8 (Δ%) | 0 | 0 | −4.7 ± 0.6 | −10.2 ± 1.1 | −22.9 ± 1.2 | −43.5 ± 2.2 | −58.6 ± 1.8 | −65.8 ± 1.2 |
| Drug | N (μg/kg/min) | 0.03 | 0.1 | 0.3 | 1 | 3 | 10 | 30 | |
| Nitro-glycerin | 8 (Δ%) | 0 | 0 | −1.0 ± 1.0 | −7.5 ± 3.2 | −16.4 ± 4.4 | −24.7 ± 4.4 | −27.6 ± 5.2 (N = 7) | |
| Drug | N (μg/kg/min) | 0.03 | 0.1 | 0.3 | 1 | 3 | 10 | | |
| PG $E_1$ | 8 (Δ%) | 0 | 0 | −1.9 ± 1.9 | −9.8 ± 3.1 | −26.2 ± 4.0 | −48.0 ± 2.7 | | |

Heart Rate

| Drug | N (μg/kg/min) | 1 | 3 | 10 | 30 | 100 | 300 | 1000 | 3000 |
|---|---|---|---|---|---|---|---|---|---|
| Ap4A | 8 (Δ%) | 0 | 0 | 1.3 ± 0.6 | 2.7 ± 0.8 | 2.4 ± 1.0 | −6.6 ± 1.2 | −15.9 ± 1.9 | −24.9 ± 2.4 |
| Drug | N (μg/kg/min) | 0.03 | 0.1 | 0.3 | 1 | 3 | 10 | 30 | |
| Nitro-glycerin | 8 (Δ%) | 0 | 0 | −0.3 ± 0.5 | −1.5 ± 1.1 | −6.5 ± 2.3 | −13.9 ± 4.0 | −13.8 ± 4.7 (N = 7) | |
| Drug | N (μg/kg/min) | 0.03 | 0.1 | 0.3 | 1 | 3 | 10 | | |
| PG $E_1$ | 8 (Δ%) | 0 | 0 | −0.3 ± 0.3 | −1.2 ± 1.4 | −8.0 ± 3.4 | −13.6 ± 2.9 | | |

The blood pressure was gradually decreased by an administration of 10 μg/kg/min or more of Ap4A, and about 40% fall in blood pressure was attained at an administration of 300 μg/kg/min. For attaining about 60% or more fall in blood pressure, a rapid and high dose of 1000 μg/kg/min or more was required. A significant decrease of heart rate was observed at about 60% fall in blood pressure. There was no problem with respect to the heart rate up to about 40% fall in blood pressure.

Furthermore, Ap4A did not significantly change the blood pressure attained by each dose. This suggests that Ap4A has a stable hypotensive effect. These results were almost the same as those for the dogs. This suggests that Ap4A is an agent which causes little tachyphylaxis.

In a test similar to the above, each of Ap4A, PG $E_1$, and nitroglycerin was administered to rats, so that about 65% fall in blood pressure, about 55% fall in blood pressure, and about 35% fall in blood pressure were stepwise attained. With respect to each agent, the recovery of blood pressure was tested. The results are shown in FIG. 1.

When the blood pressure before the administration of each agent is supposed 100% for reference, in the case of Ap4A, about 70% blood pressure was recovered in 1 minute, about 90% in 5 minutes, and the initial 100% blood pressure in 10 minutes. Thereafter, the 100% blood pressure was maintained.

In contrast to this, in the case of PG $E_1$, about 85% blood pressure was recovered in 15 minutes, but a much longer time was required to recover the initial blood pressure. In the case of nitroglycerin, a plateaus was reached by about 85% blood pressure and no complete recovery was attained.

Example 2

[Effects of Ap4A on Cerebral Blood Flow]

Male SD rats (Charles River Japan Inc.) were anesthetized with intravenous urethane (0.5 g/kg)+α-chloralose (80 mg/kg).

A femoral artery was catheterized to monitor the blood pressure and heart rate, while a femoral vein was catheterized for the aministration of each of the test drugs.

The head of each rat was fixed to a brain position fixing device and a hole was made at a top portion of the cranium. A laser blood flow probe was mounted on the cranium so as to touch the surface of the cerebral cortex through the hole, whereby the cerebral blood flow thereof was measured. A predetermined amount of Ap4A was applied by bolus injection and by infusion. The results are shown in Table 5 and FIG. 2.

TABLE 5

Effects of Ap4A by bolus injection on blood pressure (B.P.), heart rate (H.R.) and cerebral blood flow (C.B.F.) in anesthetized rats

| Dose (n) | B.P. Δ% | H.R. Δ% | C.B.F. Δ% |
|---|---|---|---|
| 0.1 μg/kg (1) | 0 | 4.0 | 2.7 |
| 0.3 μg/kg (1) | 0 | −7.0 | 7.9 |
| 1 μg/kg (3) | 5.0 ± 2.9 | 10.3 ± 10.1 | 9.3 ± 2.5 |
| 3 μg/kg (5) | −6.2 ± 5.0 | 4.6 ± 3.4 | 10.0 ± 2.0 |
| 10 μg/kg (7) | −9.9 ± 4.6 | 3.2 ± 2.0 | 21.7 ± 6.0 |
| 30 μg/kg (7) | −23.2 ± 3.5 | 6.4 ± 1.2 | 16.8 ± 3.5 |
| 100 μg/kg (7) | −34.4 ± 2.5 | 7.4 ± 3.5 | 15.8 ± 4.0 |
| 300 μg/kg (7) | −40.5 ± 5.2 | 10.9 ± 4.5 | 9.8 ± 4.0 |
| 1 mg/kg (7) | −50.4 ± 1.4 | 7.4 ± 6.0 | 8.5 ± 3.4 |
| 3 mg/kg (7) | −54.0 ± 2.5 | 6.2 ± 21.1 | 23.7 ± 9.3 |
| 10 mg/kg (7) | −63.5 ± 5.6 | −78.8 ± 2.7 | 46.3 ± 11.5 |
| 30 mg/kg (6) | −60.7 ± 7.0 | −283.2 ± 39.8 | 34.0 ± 16.9 |

Results were represented as the Δ percent from the pretreatment value. Each value indicates mean ±S.E.

Table 5 shows the effect of Ap4A by bolus injection on blood pressure (B.P.), heart rate (H.R.) and cerebral blood flow (C.B.F.) in the anesthetized rats. The results shown in Table 5 indicate that an increase in cerebral blood flow (C.B.F.) appears only when a large amount of administration of Ap4A. There is no strict relationship between the effect and the administration mount, but there is a tendency for C.B.F. to increase in a dose-dependent manner. When about 20–40% fall in blood pressure was attained, about 10–20% increase in C.B.F. was observed.

The same effects were also observed in the continuous administration of Ap4A as shown in FIG. 2.

Example 3

[Protective effects of Ap4A on deoxygenation-induced cardiac damage.]

Deoxygenation-induced cardiac damage according to the method of Aronson & Serlich (Toxical. appl. Parmac. 38, 479–488, 1976) with slight modifications. Male SD rats (Charles River Japan Inc.) weighing 320 to 390 g were anesthetized with ether, and heart quickly isolated. The isolated rat heart was mounted and perfused with Krebs-Henselite solution (118 mM NaCl, 4.7 mM KCl, 2.5 mM $CaCl_2$, 1.2 mM $MgSO_4$, 1.2 mM $KH_2PO_4$, 25 mM $NaHCO_3$ and 10 mM glucose) bubbled with 95% $O_2$+5% $CO_2$ at a flow rates of 14 ml/min. at 37° C. The myocardial function was monitored by the left ventricular pressure (L.V.P.), differential values of L.V.P. (dp/dt), heart rate (H.R.) and perfused pressure (P.P.) through a branch of an aortic canula mounted on the heart. After equilibrate for 40 min., global ischemia was produced by stopping the perfusing solution and the heart was incubated for 33 min. in 50 ml Krebs-Henselite bubble with $N_2$ gas (control). 33 min. later, the buffer solution was removed. The perfusion was re-started, and the myocardial function was measured. The heart was incubated in Krebs-Henselite solution containing Ap4A $1 \times 10^{-4}M$ during global ischemia.

Example 4

[Inhibitory and dispersing effects of $Ap_4A$ to rabbit platelet aggregation.]

Fresh blood samples were collected from male Japanese white rabbits weighing 2-3 kg. Blood was anticoagulated with citric acid (1 ml 3.8% citric acid solution +9 ml blood). These samples were centrifuged at room temperature for 20 min at 200×g to obtained platelet-rich plasma (PRP). Furthermore, the supernatant liquid was centrifuged for 10 min at 1500×g to obtained platelet-poor plasma (PPP). Aggregation of platelests was measured photometrically in a Nihon Kohden hema tracer equipped with a mechanical stirring device and with a chart record. At this time, the chart recorder was calibrated as follows: the light transmission obtained with PPP was set as 100% transmission and the optical density of PRP was taken as 0% transmission. Maximal aggregation, i.e. the maximal change in optical density of the primary wave calculated in percent light transmission. From the study, it was determined that ADP, Ap3A, PAF(platelet activating factor) and collagen induced maximal aggregations at a concentration of $1 \times 10^{-5}M$, $1 \times 10^{-4}M$, $1.9 \times 10^{-7}M$ and 5 μg/kg, respectively. In the following studies, these aggregating agents were used at maximal dose. The effect of Ap4A on platelet aggregation by ADP and Ap3A were tested. In this time, Ap4A was pretreated for 1 or 10 min before the addition of aggregating agents. Also, after the platelet aggregation was induced by addition of ADP, PAF or collagen to PRP, the platelet aggregate dispersing effect of Ap4A was tested.

Table 6 and FIG. 5 show the results of the anti-platelet aggregating effect and platelet aggregate dispersing effect of Ap4A, respectively. Both ADP- and Ap3A-induced platelet aggregations were inhibited by pre-treatment of the platelets with Ap4A. The Ap4A-induced anti-platelet aggregating effect reached at sub-maximal responses within 1 min. Both ADP- and PAF-induced platelet aggregations were dispersed after loading Ap4A on the incubated platelets. These results show that Ap4A improves the microcirculatory disturbance.

Results were shown in FIG. 3 (untreated with Ap4A) and FIG. 4 (treated with Ap4A). Treatment with Ap4A $1 \times 10^{-4}M$, significantly prevented cardiac damage (loss of L.V.P., dp/dt and H.R.) induced by deoxygenation. This result suggests that Ap4A is an anti-ischemic drug.

TABLE 6

| Inhibitory effect of Ap4A on rabbit platelet aggregation induced by ADP ($1 \times 10^{-5}M$) and Ap3A ($1 \times 10^{-4}M$) | | | |
|---|---|---|---|
| | | Ap4A $IC_{50}$ | |
| Drugs | N | 1 min. | 10 min. |
| ADP | 4 | $2.05 \times 10^{-4}M$ | $4.20 \times 10^{-5}M$ |

TABLE 6-continued

| Inhibitory effect of Ap4A on rabbit platelet aggregation induced by ADP ($1 \times 10^{-5}M$) and Ap3A ($1 \times 10^{-4}M$) | | | |
|---|---|---|---|
| | | Ap4A $IC_{50}$ | |
| Drugs | N | 1 min. | 10 min. |
| Ap3A | 4 | $(2.63 - 1.62 \times 10^{-4}M)$ $9.06 \times 10^{-6}M$ $(11.3 - 7.21 \times 10^{-6}M)$ | $(5.73 - 3.10 \times 10^{-5}M)$ $4.99 \times 10^{-5}M$ $(6.88 - 3.14 \times 10^{-5}M)$ |

Example 5

[Inhibitory effect of Ap4A on rabbit erythrocyte crenation induced by A23187.]

Fresh blood was collected from Japanese white rabbits weighing 2-3 kg. Blood samples were anticoagulated with citric acid (1 ml 3.8% Citric acid solution + 10 ml blood). These samples were centrifuged at room temperature for 15 min at 1100 rpm. After centrifugation of the defibrinated blood, the upper cell layers were discarded. The erythrocytes (pellet) were washed 4 times in a medium containing; 56.6 mM Tris-HCl, pH 7.6, 100 mM NaCl, 4.6 mM KCl, 0.64 mM $MgCl_2$. The erythrocytes were preincubated with saline solution or Ap4A at 37° C for 10min and then A23187 $1 \times 10^{-6}M$ and $CaCl_2$ $5 \times 10^{-7}M$ were added to the Mixture. After incubation at 37° C. for 20 min, the reaction mixture was centrifugated at 1000 rpm for 10 min. The precipitation was fixed by addition of 0.1M cacodylate buffer containing 0.22M sucrose. The number of transforming erythrocytes was counted using a microscope.

Table 7 shows the result from A23187-induced erythrocyte crenation and influence of Ap4A on the erythrocyte crenation. A23187-induced rabbit erythrocyte crenation was inhibited by treatment of the erythrocytes with Ap4A. This result shows that Ap4A improves the microcirculatory disturbance.

TABLE 7

| Effect of Ap4A on rabbit erythrocytes crenation induced by A 23187 | | | | |
|---|---|---|---|---|
| Compound | Concentration (M) | Crenation (%, x ± SE) | Inhibition (%) | $IC_{50}$ (M) |
| Control | | 56.6 ± 4.5 | — | |
| Ap4A | $10^{-5}$ | 49.1 ± 3.9 | 13.3 | |
| | $10^{-4}$ | 37.0 ± 6.4* | 34.6 | $3.0 \times 10^{-4}$ |
| | $10^{-3}$ | 19.2 ± 9.1** | 66.1 | |

*: $P < 0.05$
**: $P < 0.01$ as compared with the control group.

What is claimed is:

1. A method of inducing deliberated hypotension in a surgical patient comprising administering an effective amount of diadenosine 5',5'''-p¹,p⁴-tetraphosphate (I):

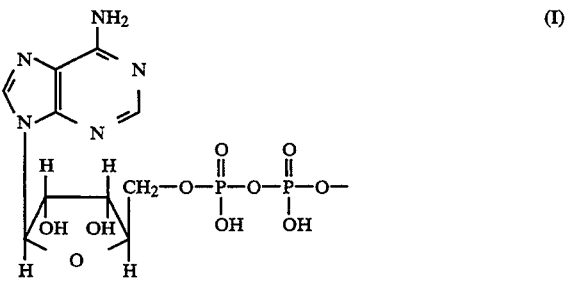

-continued

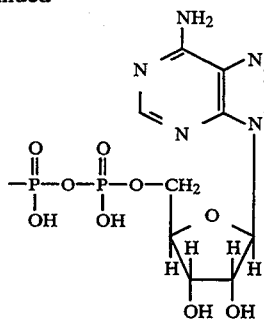

or a pharmaceutically acceptable salt thereof.

2. The method according to claim 1, wherein said effective amount is an amount sufficient to decrease the mean blood pressure of human and other mammals to less than 50% of the mean blood pressure thereof.

3. The method according to claim 1, wherein said compound of the Formula (I) is admixed with a pharmaceutically acceptable carrier or diluent.

* * * * *

UNITED STATES PATENT AND TRADEMARK OFFICE
CERTIFICATE OF CORRECTION

PATENT NO. : 5,380,715
DATED : January 10, 1995
INVENTOR(S) : SEKINE, ET AL.

It is certified that error appears in the above-indentified patent and that said Letters Patent is hereby corrected as shown below:

Column 2, line 54, "5, 5'''-tetraphosphate", should read --5, 5'''-p$^1$,p$^4$-tetraphosphate--.

Column 8, Table 2, Heading at line 59

"prostaglandin D$_1$", should read --prostaglandin E$_1$--.

Column 9, Table 2, Heading at line 2

"prostaglandin D$_1$", should read --prostaglandin E$_1$",--.

Signed and Sealed this

Ninth Day of July, 1996

Attest:

BRUCE LEHMAN

Attesting Officer

Commissioner of Patents and Trademarks